United States Patent [19]

Baratta

[11] Patent Number: 5,431,062
[45] Date of Patent: Jul. 11, 1995

[54] INTEGRAL BENDING MOMENT ABSORBER SYSTEM FOR MECHANICAL TESTING OF MATERIALS

[76] Inventor: Francis I. Baratta, 138 Ridge St., Arlington, Mass. 02174-1737

[21] Appl. No.: 242,303

[22] Filed: May 13, 1994

[51] Int. Cl.⁶ .............................................. G01N 3/02
[52] U.S. Cl. ........................................................ 73/856
[58] Field of Search ................. 73/826, 830, 831, 834, 73/856, 860

[56] References Cited

U.S. PATENT DOCUMENTS

| | | | |
|---|---|---|---|
| 3,572,102 | 3/1971 | Baratta | 73/856 |
| 4,114,420 | 9/1978 | Browning | 73/826 |
| 4,393,716 | 7/1983 | Clark et al. | 73/856 |
| 4,686,860 | 8/1987 | Liu | 73/856 |
| 4,866,992 | 9/1989 | Rice et al. | 73/856 |
| 5,105,626 | 4/1992 | Gonczy et al. | 73/826 |
| 5,138,887 | 8/1992 | Pohl | 73/856 |
| 5,286,108 | 2/1994 | Whatley et al. | 73/826 |
| 5,297,441 | 3/1994 | Smith et al. | 73/860 |

FOREIGN PATENT DOCUMENTS

| | | | |
|---|---|---|---|
| 227659 | 1/1969 | U.S.S.R. | 73/856 |
| 0596858 | 3/1978 | U.S.S.R. | 73/831 |

*Primary Examiner*—Richard E. Chilcot, Jr.
*Assistant Examiner*—James M. Olsen
*Attorney, Agent, or Firm*—Jeffrey D. Marshall

[57] ABSTRACT

An apparatus is invented that accurately determines the failure or fracture stress of materials that behave in a brittle manner while under static or dynamic loadings that applies a stress to a test specimen in tension, compression, shear, or combination thereof, or in the case of cyclic loading stressing a fatigue sample. The bending and twisting of the test specimen due to the inherent misalignments in conventional test systems are drastically reduced by this device, which utilizes a hollow cylinder, termed a bending moment absorber whose ends are fitted and fixed to the ends of a dumbbell or flat specimen. This assembly, in turn, is clamped at each end by commercially available hydraulically-operated grips within the load train. This device causes the combined cross-sections of the hollow cylinder and the specimen to act in concert so as to markedly increase the moment of inertia of the system and thus reduce both the imposed bending stress and the error during testing. If the bending moment absorber and the specimen are of dissimilar materials and their modulus of elasticity ratio is less than 1.0, while their fracture strength ratio is greater than their modulus ratio, then failure will occur in the specimen, and the moment absorber will be reusable. In addition, this apparatus can be operated at cryogenic, ambient, or elevated temperatures.

23 Claims, 7 Drawing Sheets

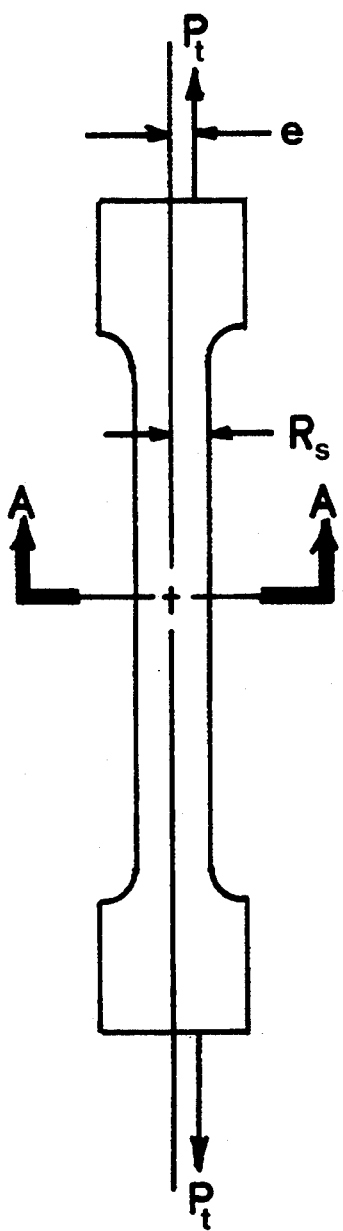
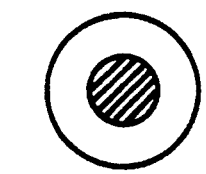
VIEW A-A
FIG. 1B
FIG. 1A

VIEW A-A

VIEW B-B

VIEW A-A

VIEW A-A

VIEW A-A

VIEW A-A

VIEW A-A

VIEW A-A

INTEGRAL BENDING MOMENT ABSORBER SYSTEM FOR MECHANICAL TESTING OF MATERIALS

REFERENCES CITED

U.S. Patent Documents

U.S. Pat. No. 3,572,102 Mar. 23, 1972 Baratta et al.
U.S. Pat. No. 4,686,860 Aug. 18, 1987 Liu

Other Publications

"Method of Tensile Testing of Brittle Materials," R. Sedlacek, and F. A. Holden, Review of scientific Instruments, Vol. 32, 1962.

"A New Axial Tension Tester for Brittle Materials," F. I. Baratta, and G. W. Driscoll, Army Mechanics Research Center, AMMRC TR 69-02, 1971.

"Tensile Testing of Ceramic Materials—A New Approach," L. Hermanson, J. Alderborn, and M. Burstrom, in *High Tech Ceramics*, ed. P. Vincenzini, Elssevier Science Publishers, 1987.

MTS Testing News, Vol. V. No. 11, 1987.

ASTM Designation: E 1012-89, "Standard Practice for Verification specimen Alignment Under Tensile Loading."

MTS Publication Notes, 1993.

Instron Corporation Brochure WB-1005.

FIELD OF INVENTION

This invention solves the problem and need for a simple method of accurately determining mechanical properties of materials that behave in a brittle manner. This is accomplished by minimizing the effect of the inherent misalignments, which cause undesirable bending moments in the specimen, resulting in large errors in the mechanical property determination. The objective is attained by surrounding the specimen with a hollow tube, called a bending moment absorber, which is closely fitted and fixed to the ends of the specimen, and this assembly is tightly clamped by commercially available hydraulically-operated grips to ensure intimate contact between the tube and the specimen during the application of load. Thus, the bending moment is absorbed by the hollow tube, since it has a much larger moment of inertia than that of the specimen. This results in a markedly reduced error in the determination of mechanical properties of those materials that behave in a brittle manner.

SUMMARY

Attempts to determine the desired mechanical properties of materials that behave in a brittle manner without precautionary measures to reduce the applied load misalignments, no matter how slight, will result in extreme errors. Such errors arise because of the inherent misalignments in the testing machine, the specimen holders or gripping devices, and asymmetrical machining of the specimen itself. Usually these initial misalignments cause little problem when testing nonbrittle metallic materials, because as the material is stressed it plastically deforms locally at points of contact with the specimen holders or grips, and aligns itself within the testing system; thus, fairly accurate results ensue. However, materials that behave in a brittle manner do not locally deform and the initial misalignments persist throughout the complete test, resulting in large errors. The magnitudes of these errors are dependent upon the initial misalignments and the configuration of the specimen to be tested.

This invention presents an improved method of determining mechanical properties of materials that behave in a brittle fashion. The improvement is realized by increasing the moment of inertia of the system by fixing the ends of the specimen within a thin hollow tube, termed here a bending moment absorber. This assembly is mechanically clamped at its large ends by commercially available hydraulically-operated grips within the load train. In this way the bending stress is reduced to the specimen and is absorbed by the the hollow tube, thus reducing the error in the determination of mechanical properties of those materials that behave in a brittle manner.

The invention can accommodate a round dumbbell type specimen, which can be either pinned or threaded and/or bonded at its ends to the bending moment absorber, or the sample can also be a flat specimen, wherein semi-cylindrical spacers are employed at each end and pinned or threaded and/or bonded between the specimen and the bending moment absorber. Also, if the modulus of elasticity of the bending moment absorber is less than that of the specimen, while their fracture strength ratio is greater than their modulus ratio, then failure will occur in the specimen and the absorber will be reusable.

The device can be readily adapted to commercially available ancillary testing equipment and instrumentation such that it can operate at cryogenic, room, midrange and at extremes of elevated temperatures and still allow the determination of stress-strain data and failure strength of materials.

BACKGROUND OF THE INVENTION AND PRIOR ART

Background

The selection of a material for a particular structural application depends on its mechanical properties. There are a number of standard tests that measure properties specifically designed to yield required engineering design data. For example, one of the most convenient types of strength tests to analyze is the tensile test where the specimen is loaded in uniform uniaxial tension. Tension tests are also conducted using ancillary equipment and instruments at a range of temperatures, such as cryogenic, ambient and above. From such tests, various mechanical properties of metallic materials needed for design applications can usually be gleaned without too much difficulty, except for several specialized tests mentioned below. However, attempts to determine the desired mechanical properties of materials that behave in a brittle manner without precautionary measures to reduce the applied load misalignments will result in extreme errors. This is because materials that behave in a brittle manner do not realign any small inherent eccentricity and the resulting bending stress will not only be amplified but also will be superimposed on to the axial stress during testing. Thus, the error will be extreme (this is mathematically shown in Error Estimates presented below), and premature failure will occur.

The effects of misalignment on the stresses and strains measured in studies of fracture strength of materials in a brittle state, not only in the testing of tensile specimens but also compression, and torsion specimens, as well as combinations thereof; and including cyclic fatigue specimens, need to be mentioned. These effects can also be present in ductile metallic materials when testing for stress-rupture life, creep, fatigue life, plastic microstrain, alloy strengthening, surface-sensitive strength, fracture of notched-tensile specimens and, precracked-notched-tensile specimens.

Most of the following section, except for some minor alterations, was taken directly from ASTM Designation: E 1012-89, "Standard Practice for Verification of Specimen Alignment Under Tensile Loading."

Source of Misalignment

The usual procedure in testing in uniaxial tension and cyclic fatigue is to apply a tensile load to a specimen through grips attached to a loading train and then correlate the strain response of the specimen, as measured with an appropriate extensometer, with applied stress. A similar approach is taken with compression specimens, except compression platens are used rather than tensile grips. To eliminate the bending moment entirely, and thus the error, would require ideal alignment.

However, this is impossible to achieve because the top and bottom grip centerlines have to be precisely in line with one another and with the centerline of other components of the load train. Moreover, they have to be precisely in line with the specimen centerline. Finally, the specimen has to be symmetrical about its centerline. Departures from the ideal situation are unavoidable and are caused by poor alignment of the top and bottom grip centerline, poor conformance of specimen centerline to top and bottom grip centerlines, and asymmetrical machining of the test specimen itself.

The objective of any effort to improve alignment is to bring the centerlines of all components of the loading train into alignment as close as possible with one another. Logically the first piece of hardware on which to focus attention is the testing machine itself. Testing machines as-received from manufacturers may have deviations between top and bottom grip centerline positions of 0.001 to 0.125 in. (0.03 to 3.18 mm). Moreover, further misalignment may develop as loads are applied causing additional machine frame deflection or as non-axial crosshead separation occurs. In the worst case, deviations in this range have been reported to lead to eccentricities resulting in a 50 to 100% difference between extreme surface bending strain and average strain.

After the testing machine comes a consideration of the tolerances specified for the machining of the load train components and test specimens. In ordinary machine shop practice, tolerance usually range from ±0.002 to ±0.010 in. (±0.05 to ±0.25 mm). These tolerances may cause poor alignment when the components are assembled, for example, in the worst case, these tolerances have been reported to lead to eccentricities resulting in a 50 to 100% difference between extreme surface bending strains and average strain.

Error Estimate

As mentioned above, it is impossible to precisely align all of the components in the load train. Even if the forces are only slightly misaligned, bending and/or twisting of the specimen will cause premature failure and an excessive error in determining the fracture strength of materials that behave in a brittle manner. In order to demonstrate the magnitude of such an error, consider as an example, the error associated with the usual tension or compression testing system utilizing a brittle round dumbbell specimen, shown in FIG. 1A, where e is the eccentricity within the testing machine, the grips and the asymmetry caused by the machining tolerances of the specimen; Pt is the total applied force from the testing machine and Rs is the gage-section-radius of the specimen. For convenience only the tension case, as shown in FIG. 1A, is considered. However, that which follows is equally applicable to compression and fatigue mode of loading, as well, and with some minor modifications to torsion loading.

The axial stress Ss in the specimen gage section is simply:

$$Ss = Pt/As \tag{1}$$

Where Pt is the total applied force from the testing machine, and As is the area of the specimen cross section having a radius at the gage section of Rs.

The bending stress Sb is approximately:

$$Sb = Mc/I \tag{2}$$

Where M is the bending moment equal to Pt multiplied by e; e being the eccentricity due to misalignment in the loading system and within the specimen, c is the distance from the centroid of the gage cross section or neutral axis to the outer surface of the cross section, i.e., c = Rs, and I is the cross-sectional moment of inertia, which is:

$$I = \pi Rs^4/4 \tag{3}$$

Substitution of these relationships into equation 2 gives:

$$Sb = 4Pt\, e/(\pi Rs^3) \tag{4}$$

The bending stress divided by the axial stress approximates the error that will occur during testing of a brittle material; therefore, the percent error is $$\% \text{ Error} = (4e/Rs) \times 100 \tag{5}$$

As an example of the effect of the eccentricity on the error in determining the fracture strength of a brittle tension test specimen consider only one factor, the eccentricity of a commercial testing machine. Although as stated above, this eccentricity can range from 0.001 to 0.125 in. (0.03 mm to 6.35 mm), nevertheless, consider allowing it to be only half of the maximum, i.e., 0.0625 in. (1.59 mm). If the specimen gage section radius is 0.250 in. (6.35 mm) then the error will be 100%, according to equation 5. Note that only one factor, the testing machine eccentricity was taken into account; had all factors been considered the total error would have been much greater. Also, if Rs<0.250 in. the error would have been even greater.

PRIOR ART

There have been a number of attempts to circumvent or reduce the effect of load misalignment on mechanical property determination for those materials that behave in a brittle manner. However, not all of the methods that have been devised will be described here; but only those that are pertinent to the background discussion.

Pressure Devices

There are several devices that utilize fluid pressure to bypass the problems associated with either the application of an applied load using a testing machine, and/or the load train and specimen grips, etc. The following is a brief description and critique of such attempts:

The Stanford Institute Burst Test utilizes a thin ring-shaped test specimen which is subjected to internal hydraulic pressure acting radially through an inner rubber bulb; this causes a tangential tensile stress in the specimen wall. Knowledge of pressure at failure, specimen dimensions, and equilibrium of forces allows the determination of tensile strength of the brittle material, see "Method of Tensile Testing of Brittle Materials," R. Sedlacek and F. A. Holden, Review of Scientific Instruments, Vol. 33, 1962. The disadvantage associated with this costly test method is that it requires specially designed test equipment that necessitates a complicated test set-up. also, since the test specimen is a thin hollow cylinder, it requires a large initial blank of material for the finished sample. Additionally, testing can only be accomplished at or near ambient temperatures.

Another hydraulic pressure device, referred to by its authors as the Brittle Axial Tension Tester (BATT), see "A New Axial Tension Tester for Brittle Materials," by F. I. Baratta and G. W. Driscoll, Army Mechanics Research Center, AMMRC TR 69-02, Aug. 1971, was also conceived to determine the tensile strength of brittle materials. This device is comprised of a hollow cylinder with two O-rings retained in grooves at a predetermined distance located in the inner wall of the hollow cylinder. Upon inserting the round dumbbell shaped test specimen into the cylinder, the O-rings engage and form a seal around the larger end diameters of the specimen. Pressure applied via a fluid between the end diameters through a port in the middle of the cylinder produces an axial-tensile force in the specimen gage section. Although the fluid produces a biaxial radial pressure around the specimen it is small compared to the axial stress, because of the large ratio of the diameter of the specimen ends to that of the gage section.

Continuous monitoring of the pressure is maintained up to specimen failure. The tensile strength of the material is based on the knowledge of the pressure, the cross-sectional area of the specimen gage section and from conditions of equilibrium of forces. The major advantage of the BATT device is that it is self-aligning, except for the small eccentricity due to specimen machining tolerances. However most of the other problems induced by misaligned loadings previously mentioned are eliminated, so that a marked improvement in the accuracy of the fracture data is realized. Nevertheless, the disadvantage is that testing can be done only at or near ambient temperature.

ASCERA Corporation, of Robertsfors, Sweden, modified the BATT test described above by simplifying the specimen, namely, a straight cylindrical rod, which is the gage section of the specimen; this is bonded at its ends to two steel pistons by a high strength structural adhesive, see "Tensile Testing of Ceramic Materials—A New Approach," Hermanson, et al., in HIGH TECH CERAMICS, ed. P. Vincenzini, Elssevier Science Publishers, 1987. The assembly allows this composite, which is a dumbbell shaped specimen, to be inserted between two O-rings, and as in the BATT test, pressure is introduced between the piston heads. The major problem with this device is that tests yield low usable results due to a large percentage of failures occurring near or at the specimen-steel-piston interfaces. Also, as in the BATT test, this method can only be employed at or near ambient temperature.

Another device, called the Southern Research Air Bearing Test, incorporates gas bearings via hemispherical seats at each end of the load train to provide concentricity of the load in the testing machine, see C. C. Pears and F. J. Digesu, "Gas Bearing Facilities for Determining Axial Stress-Strain and Lateral Strain of Brittle Materials to 5500° F.," presented at the Annual Meeting of ASTM, Chicago, Ill., 1962 This device minimizes the inherent eccentricity due to the testing machine misalignment, but not those that arise because of specimen gripping eccentricities and specimen machining tolerances. Another serious disadvantage of this device is that its initial fabrication cost is high.

A more recent tensile testing device, which provides a self-aligned hydraulic piston assembly for tensile testing of ceramic materials, is described in U.S. Pat. No. 4,686,860. The abstract from the patent specification is as follows:

The present invention is directed to a self-aligning grip housing assembly that can transmit a uniaxial load to the specimen without introducing bending stresses into the specimen. Disposed inside said grip housing assembly are a multiplicity of support pistons connected to a common source of pressurized oil that carry equal shares of the load applied to the specimen regardless whether there is initial misalignment between the specimen load column assembly and housing axis.

The major disadvantage of this device, like the gas bearing test system described above, is that it is very costly to manufacture because of the complex design requiring eight hydraulic pistons in each end assembly. Also the button head specimens dictate elaborate collar type grips. Nevertheless, this invention has been commercialized by Instron Corporation, see their brochure WB-1005.

MTS Systems Corporation, another manufacturer of mechanical testing machines and ancillary equipment, also has marketed a pressure type testing device for brittle materials, see MTS Testing News, Vol. V, No. 11, Fall 1987. It uses essentially the same principle as that employed above by Instron Corporation, except there is only one pressurized cylinder at each end of the load train rather than eight described in U.S. Pat. No. 4,686,860. It is claimed that the bending moments in the load train are minimized because of equalization of the forces within the pressurized cylinder. Again, the major disadvantage of this system as with the above invention, is that it is also quite expensive to produce.

Other Mechanical Devices

There are several techniques other than the use of fluid pressure that have been employed to minimize the effect of extraneous bending moments on the accuracy of the test system:

One of these is described in U.S. Pat. No. 3,572,102. This device employs two circular end plates to which a thin hollow shell is rigidly bonded to the two end plates. Access holes are provided to allow the specimen to be held by grips attached to the inside of the assembly. The end plates in turn have external means to attach to the commercial testing machine. When a tensile load is applied the bending moment from the testing machine, due to its inherent eccentricities, is transferred to the outer shell of the assembly because of its large moment of inertia. The major disadvantage of this device is that it removes only the bending moment due to the inaccuracies of the testing machine and not those misalignments internal to the fixture due to the grips or specimen asymmetrical machining tolerances.

Another technique that attempts to minimize the effect of eccentricities and bending moments, is done by affixing strain gages to the specimen, monitoring the strain under a small preload and readjusting the position of the specimen prior to testing. This approach is employed by MTS Systems Corporation utilizing their commercially available Alignment Fixture, see MTS "Application Notes", published in 1993. This fixture according to the literature "—lets you adjust the alignment of your test system after it is fully preloaded. Four setscrews along the top of the fixture are turned to adjust load train angularity. Four setscrews along the bottom are turned to adjust concentricity." The major disadvantage here, although not stated in the published brochure, is that such methods require continuous monitoring of the strain sensors and cumbersome readjustment during testing to insure that the eccentricities are minimized.

It is seen from the above discussion that there is a need for a testing device that will result in accurate mechanical property data determination at cryogenic, ambient and elevated temperature, that is inexpensive, simple and convenient to use.

DESCRIPTION OF THE INVENTION

Materials that behave in a brittle manner that are to be tested are formed into small test specimens. These specimens are tested under static or dynamic loading. Such materials would include: ceramics, certain composites, some metallic materials, such as tungsten, beryllium, and cast iron; and even ductile metallic test specimens that have been notched and/or fatigue precracked. The forces that are applied during testing, such as: tension, compression, torque, and bending are recorded to obtain the instantaneous data and failure stress in tension, compression, shear, combinations thereof, as well as the total cycles to failure as in the case of fatigue loading. Combinations of stresses would include axial (tension or compression) and shear, or axial and bending; or axial, shear, and bending, etc., are often investigated to determine how various materials would fail under such stress combinations. Such investigations are sometimes conducted to also prove out various failure theories. However, even if the forces are only slightly misaligned and they usually are, bending and/or twisting of the specimen, i.e., the centerline of the specimen approximates an 'S' shape, can affect the results. In routine tension tests of most engineering materials, bending stresses will be insignificant if sufficient plastic flow occurs during the test, this will minimize or eliminate the bending loads.

However, when testing under conditions where plastic flow is limited by inherent brittleness of test specimen material, or by need for measurements near the elastic limit, or when plasticity is confined to a small volume (specimens with stress concentration such as notches), small misalignment may give rise to variable bending stresses which have noticeable effects on test results. Such results often lead to gross inaccuracies.

This invention describes a simple apparatus to reduce such bending or twisting of a test specimen and can be operated at: cryogenic, ambient, or elevated temperature. The apparatus utilizes a hollow cylinder surrounding the sample, termed a bending moment absorber, which is closely fitted and pinned or threaded and/or bonded to the ends of a dumbbell specimen. A flat specimen can also be tested by utilizing semi-cylindrical spacers at its ends which are then pinned or threaded and/or bonded to the bending moment absorber. These assemblies, in turn, are clamped at their ends by commercially available hydraulically-operated grips (collets for a round specimen and wedges for a flat specimen) within the load train, thus forcing the specimen to act as an integral part of the bending moment absorber. The moment of inertia of the combined cross-sections of the assembly, including the specimen is markedly increased. Since the bending moment absorber has such a large cross-sectional moment of inertia compared to that of the specimen, it absorbs a major portion of the bending moment and thereby reduces the bending or twisting of the test specimen and thus the error.

When testing in the linear mode regime, i.e., linear response of the material, the material for the bending moment absorber can be chosen to be dissimilar to that of the specimen such that the modulus of elasticity ratio of the bending moment absorber to that of the specimen is less than 1.0; while their fracture strength ratio is greater than their modulus ratio. Because the bending moment absorber and specimen are fixed to each other by pins or threaded connections the load distribution during testing is known. With the aid of appropriate instrumentation and prior knowledge of the modulus ratio, the stress at failure, which will occur in the specimen will be known, as well as stress-strain data during testing. Failure will occur in the test specimen before the bending moment absorber reaches its yield or failure stress and thus it will be reusable.

A similar approach can be adopted for testing in the nonlinear mode, i.e., testing in extremes of elevated temperatures, by heating only the specimen and cooling the encompassing bending moment absorber. Again, if the bending moment absorber and the specimen are initially of dissimilar materials and their modulus of elasticity ratio is less than 1.0; with the use of appropriate instrumentation the failure stress that occurs in the specimen and the stress-strain curve will be known. As before, the bending moment absorber will be retained for reuse.

Alternatively, the bending moment absorber can be fabricated from the same material as the specimen and this assembly heated for testing in the nonlinear mode of operation. With appropriate instrumentation the failure stress of the test material will be known.

BRIEF DESCRIPTION OF DRAWINGS

FIG. 1A shows a view of a tensile specimen under an eccentric applied force called Pt, and the eccentricity, called e, is exaggerated for demonstration purposes.

FIG. 1B Shows a cross-sectional view of FIG. 1A, shown for clarity, with the gage-section-radius of the specimen represented by Rs.

PREFERRED EMBODIMENT

The foregoing and other objects, features and advantages of the invention will be apparent from the following more particular description of preferred embodiments of the invention, as illustrated in the accompanying drawings. The drawings are not necessarily to scale, emphasis instead being placed upon illustrating the principles of the invention.

The following paragraphs describe the preferred embodiments, where the figures are discussed in detail to aid in explaining the operating proposed principle. First however, a section called Error Estimate is presented to demonstrate the operating principle by comparing the resulting reduced error to the calculated error previously shown to exist in the usual test method. Also included is a section termed Test Methods, which is subdivided into two subsections entitled Linear Regime and Nonlinear Regime. The latter two sections discuss the employment of the device in the various temperature regimes of interest and related ramifications with regard to linear and nonlinear material behavior.

The principle that allows a reduction of the error in the mechanical property determination using the present invention is mathematically demonstrated in the following:

Error Estimate

Figures 6A, 6B:
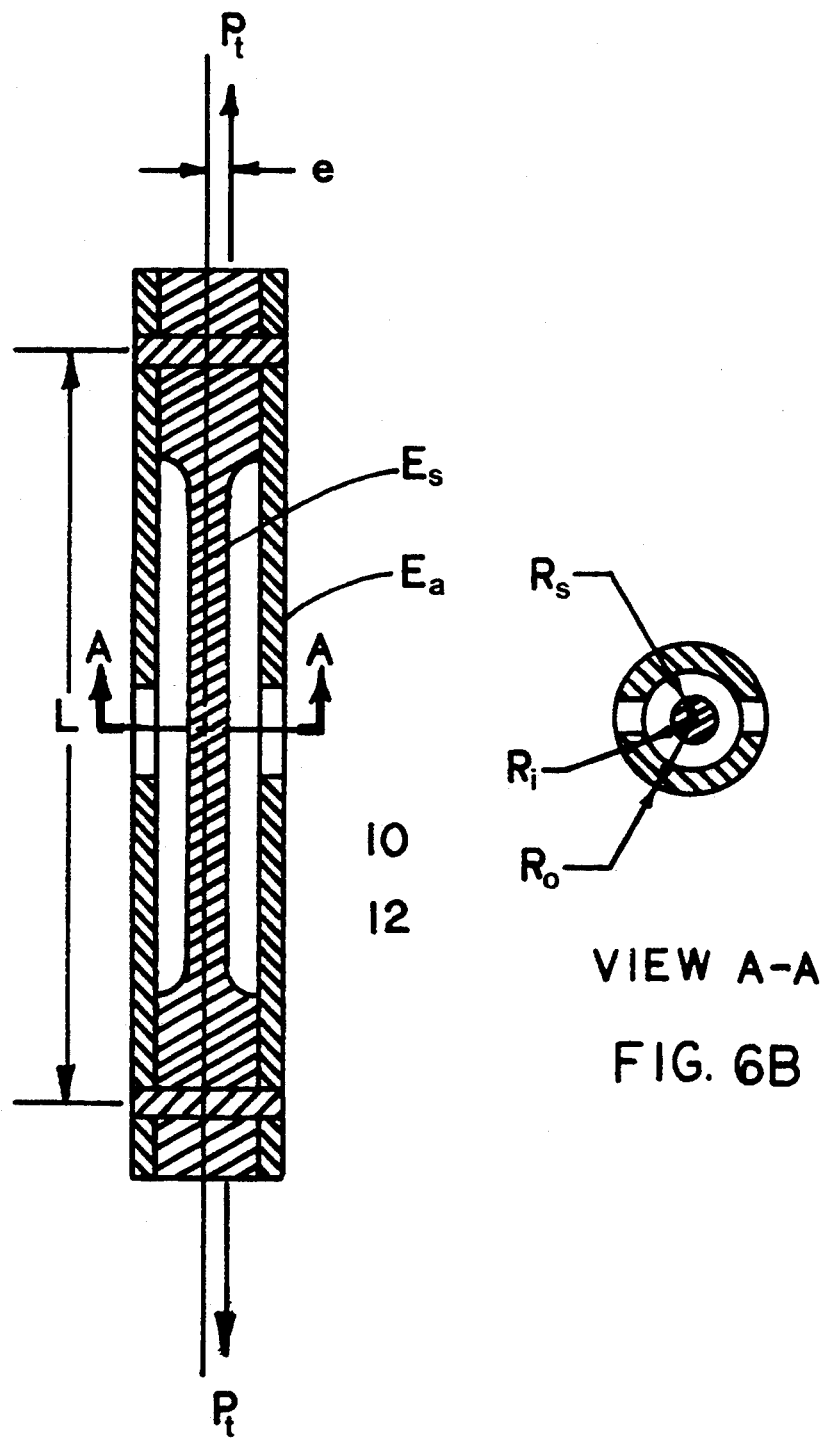
FIG. 6A shows a cross-sectional view of the bending moment absorber-assembly with an eccentric total force Pt, and an exaggerated eccentricity e. Rs, Ri, and Ro are: the gage-section-radius of the specimen, the inner radius of the bending moment absorber, and the outer radius of the bending moment absorber, respectvely.
FIG. 6B is a cross-sectional view of FIG. 6A, shown for clarity. Rs, Ri, and Ro are: the gage-section-radius of the specimen, the inner radius of the bending moment absorber and the outer radius of the bending moment absorber, respectively.

Referring to FIG. 6A and FIG. 6B, it is assumed that the connections at the bending moment absorber interfaces with the specimen are rigid, i.e., the assembly acts as one solid body. This is not completely correct in that there will be some flexibility at the interfaces, but this can only be determined by experimentation. Nevertheless, it shall be assumed that the ideal case exists, in order to simplify the mathematics and easily demonstrate the principle.

In FIG. 6A, consider the axial displacement ds of the specimen 10 and the displacement da of the bending moment absorber 12 during testing, both having a fixed length of L; $ds=L\epsilon s$ and $da=L\epsilon a$, respectively, but $ds=da$, and $L(Ss/Es)=L(Sa/Ea)$.

Also, $\epsilon s$ and $\epsilon a$ are the axial strains in the specimen and the absorber, respectively.

Thus, $$Ss/Es = Sa/Ea, \text{ or } Sa = Ss(Ea/Es) \qquad (6)$$

The total load Pt is $$Pt = Ss\ As + Sa\ Aa \qquad (7)$$

Utilizing Eq. 6, we obtain $$Pt = Ss[As + Aa(Ea/Es)] \qquad (8)$$

The bending stress in the specimen Ssb is $$Ssb = M\ c/I \qquad (9)$$

Where M is the bending moment due to the total eccentric distance e, between the centerline of the specimen gage section and the applied load from the testing machine, thus $M = Pt\ e$, and c is the distance from the neutral axis of the specimen to its outer radius, i.e., $c = Rs$. Also, I is the combined moment of inertia of the specimen and the bending moment absorber.

By substituting the appropriate values into Eq. 9, the final form for Ssb is $$Ssb = 4Pt\ e/\{Rs\ As\ [1 + (Ro/Rs^4) - (Ri/Rs^4)]\} \qquad (10)$$

Where Ri is the large radius at the specimen ends, which is also equal to the inner radius of the bending moment absorber, and Ro is the outer radius of the bending moment absorber.

The axial stress in the specimen using Eq. 7 and Eq. 8 is $$Ss = (4Pt/As)/\{1 + (Ea/Es)[(Ro/Rs^2) - (Ri/Rs^2)]\} \qquad (11)$$

Dividing Ss into Ssb will give the approximate error due to the eccentricity in the test system:

$$\% \text{ Error} = \{(4e/Rs)\{1 + (Ea/Es)[(Ro/Rs^2) - (Ri/Rs^2)]\}/[1 + (Ro/Rs^4) - (Ri/Rs^4)]\} \times 100 \qquad (12)$$

To effect a comparison of the improved reduction of the error, as before let: e be 0.0625 in. (1.59 mm), Rs=0.250 in. (6.35 mm), with Ri=0.500 in. (12.70 mm) and Ro=1.500 in. (38.10 mm). A realistic modulus ratio is 0.76. The resulting error computed from Eq. 12 is less than 2%, as compared to 100%, previously determined for the usual testing case; or an error reduction of better than 50 times.

It is noted here that there is an advantage to using a bending moment absorber of different material and of lower modulus of elasticity than that of the specimen, that is by letting Ea<Es in Eq. 6, allows the reuse of the bending moment absorber. For example, consider a typical bending moment absorber material fabricated from structural steel and the test specimen material being hot pressed silicon nitride (HPSN). The bending moment absorber has a room temperature yield strength of 100 ksi (689.5 Mpa) and the HPSN has a room temperature tensile strength of approximately 110 ksi (758.4 Mpa). The modulus of elasticity ratio Ea/Es of these two materials is approximately 0.76. When the specimen fails at a stress of 110 ksi (758.4 Mpa), the bending moment absorber is at a stress of 83.6 ksi (576.4 Mpa) and thus available for reuse. In addition, notice that in Eq. 12 the use of a modulus ratio of less than 1.0 further reduces the error in the system.

Figure 2A:
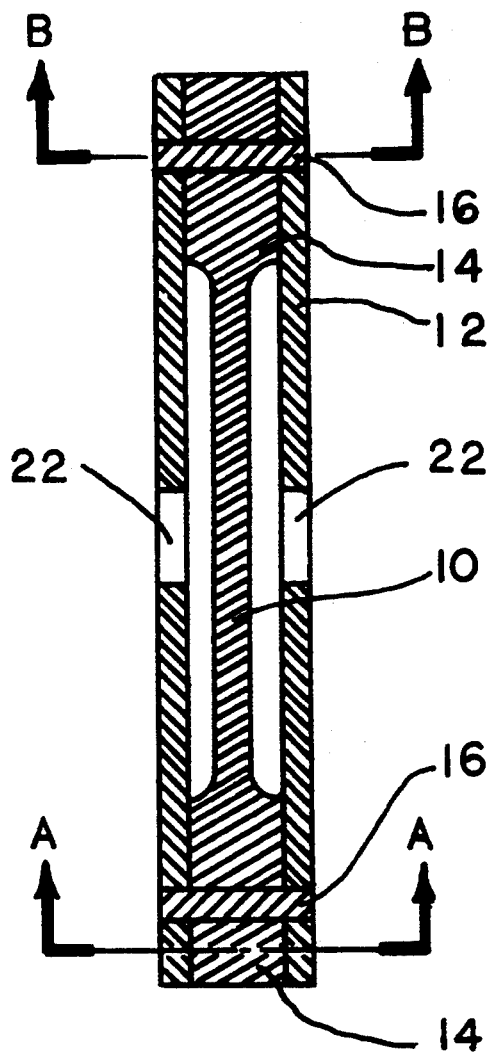
FIG. 2A is a cross-sectional view of a round dumbbell specimen shown inserted and pinned within a surrounding means, called the bending moment absorber.
Figure 2B:
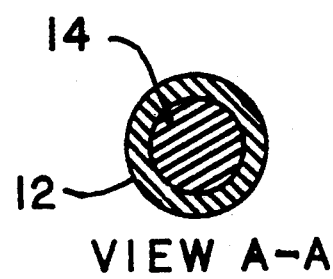
FIG. 2B is a cross-sectional end view of FIG. 2A, shown for clarity.
Figure 2C:
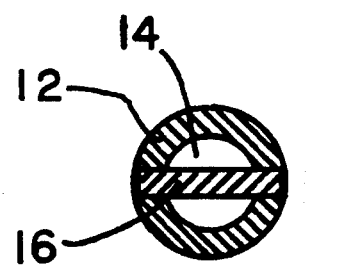
FIG. 2C is a cross-sectional view of the pin connection depicted in FIG. 2A, shown for clarity.

In FIG. 2A, FIG. 2B, and FIG. 2C a dumbbell specimen 10 is shown inserted and pinned 16 at each of its head-ends 14 within the bending moment absorber tube 12; this tubular sleeve also has ports 22 that allow deflection observations of the specimen. The bending moment absorber and the specimen are fitted snugly or even slightly shrink-fitted within each other to insure intimate contact at their interfaces. The dumbbell specimen 10, with accompanying holes for pins 16, or threaded holes for bolts or screws, can be designed within the present state-of-the art and the pin, bolt or screw material chosen, such that failure will be insured within the central gage section of the specimen design. It is noted that only the pins are shown for demonstrative purposes.

In the above described embodiment the bending moment absorber is a tube which has drilled holes at the top and bottom and a prepared sample or specimen with matching top and bottom holes is encompassed by the absorber tube. Each hole in the absorber is connected by a pin, bolt or screw (these not shown) to a matching hole in the sample. These fasteners may terminate within the sample or may be drilled through the sample and engage holes on both sides of the tube. At least one through-pin, bolt or screw or two terminating pins, bolts or screws aligned oppositely on the sample will be used at each end of the sample.

There are a number of various fastening methods other than that given above that are further described below, but for the sake of clarity are not presented in the figures:

A second embodiment where the prepared sample is slip-fitted into the bending moment absorber tube and these two components are clamped together at the top and bottom ends by mechanically activated devices, such as two drillpress chucks, or two mechanically operated collet grips; this assembly in turn is further clamped together by two hydraulically-operated grips attached to the ends of the testing machine. Alternatively, a set of hydraulically-operated grips can be used in place of the mechanically operated devices.

A third embodiment where the prepared sample is placed within a mold and or material with a very low modulus of elasticity compared to that of the specimen, such as a catalyzed elastomer for example, molded as a tube around the sample, providing grip surfaces at the top and bottom that are molded to the sample. Note that if the modulus of elasticity of the bending moment absorber is very much less than that of the the specimen, then the axial stress in the absorber approaches zero (see Eq. 6 above). It is also noted that knurled or serrated surfaces in the grip area may be used to enhance the adhesion between the elastomeric material and the sample, as long as the surface modifications have no effect on the sample or the subsequent test results.

In a fourth embodiment the surrounding tube can be a metallic, ceramic or a polymeric tubular sleeve which has an interference fit with the prepared sample. The tube is heated to an appropriate elevated temperature in an oven then slipped over the prepared specimen which is chilled. The tube is cooled causing a tight interference fit at the ends of the prepared sample, which can be fitted into a testing machine.

In a fifth embodiment, a high temperature steel, such as a superalloy, or a ceramic material can be utilized as a bending moment absorber tube, with an interference fit joining the top of the prepared sample to the top end of the tube and the bottom end of the prepared sample to the bottom end of the tube, allowing use of a bending moment absorber at high testing temperatures.

In a sixth embodiment the bending moment absorber material can be chosen to have an appropriate linear coefficient of thermal expansion compared to the test sample such that the bending moment absorber radially compresses the sample at its top and bottom ends when testing at both cryogenic and elevated temperatures.

In a seventh embodiment the bending moment absorber tube material can be chosen such that its modulus of elasticity is less than that of the prepared sample specimen. In this way the specimen during testing supports a major portion of the applied force and will fail leaving the bending moment absorber intact for reuse.

Figure 3B:
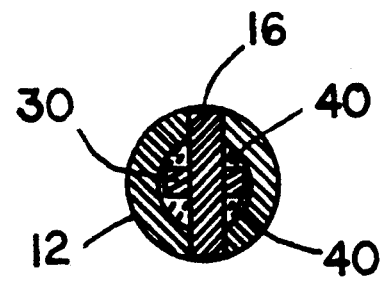
FIG. 3B is a cross-sectional view of the end of FIG. 3A, shown for clarity.
Figure 3A:
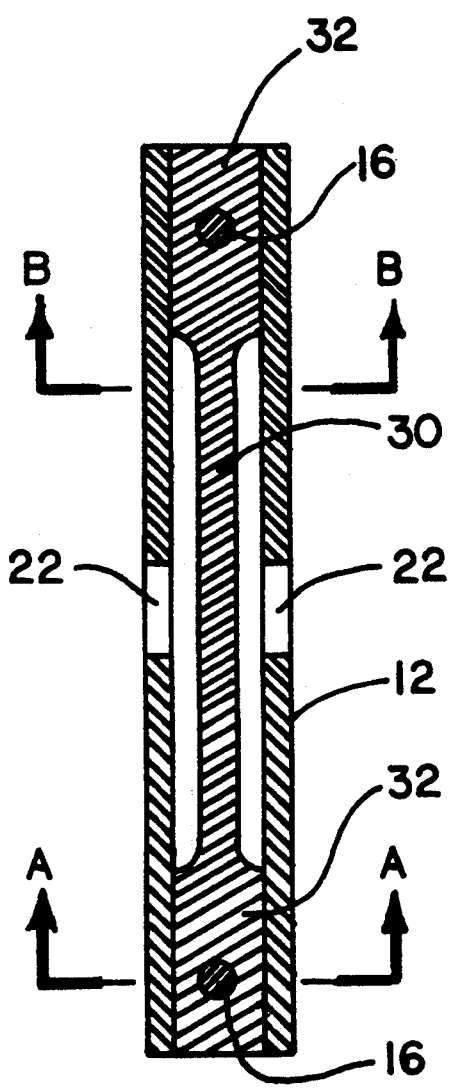
FIG. 3A is a cross-sectional view of a flat tensile specimen shown inserted and pinned with spacers within the bending moment absorber.
Figure 3C:
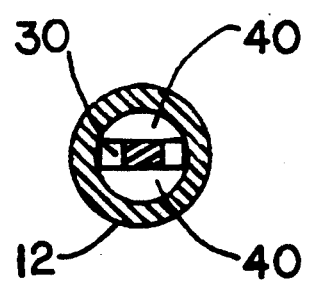
FIG. 3C is a cross-sectional view of FIG. 3A, shown for clarity.

Now looking at FIG. 3a, FIG. 3B, and FIG. 3C, which show a flat tensile specimen 30, with its head-ends 32 sandwiched between semi-cylindrical spacers 40 and inserted into and pinned 16 within the same reusable bending moment absorber tube 12, with ports 22. The bending moment absorber, the specimen and the semi-cylindrical spacers are fitted snugly or even slightly shrink-fitted within each other to insure intimate contact at their interfaces. The flat specimen 30, with the accompanying holes for pins 16, can also be designed within the present state-of-the art and the material chosen for both the pins and the semi-cylindrical spacers 40, such that failure will occur within the central section of the specimen gage section.

Figures 4A, 4B:
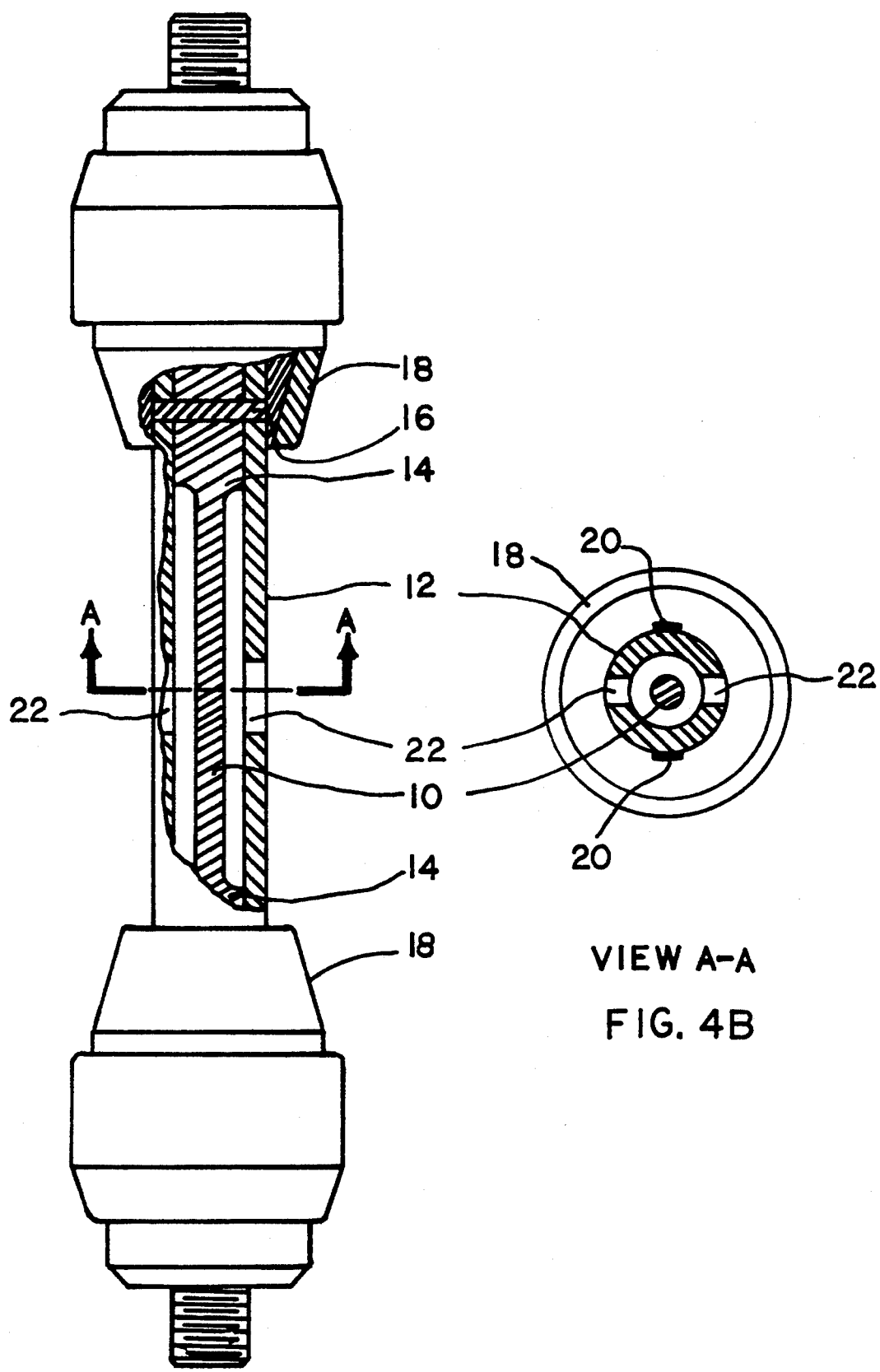
FIG. 4A is a cross-sectional view of a round dumbbell specimen shown inserted and pinned within the bending moment absorber and this assembly, in turn, is grasped at both ends by hydraulically-operated collet grips.
FIG. 4B is a cross-sectional view of FIG. 4a, shown for clarity.
Figure 7A:
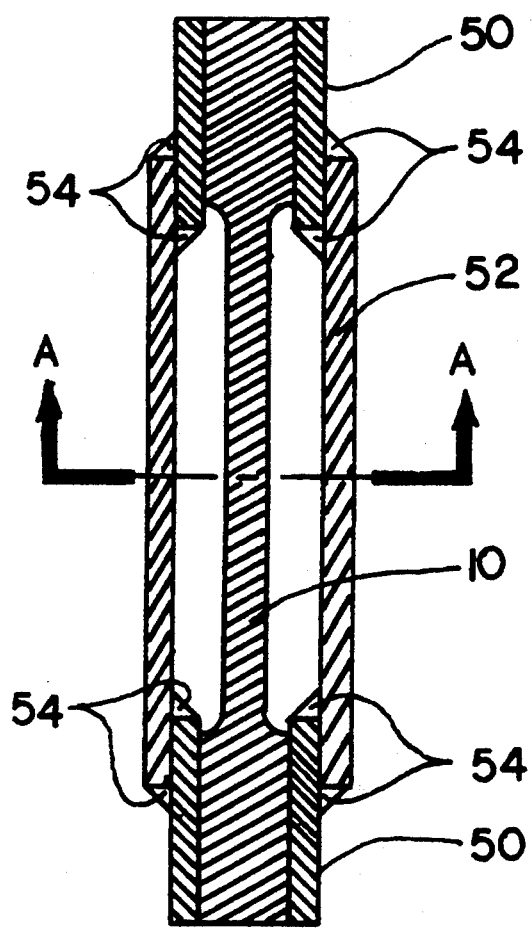
FIG. 7A is a cross-sectional view of a dumbbell specimen shown inserted and shrunk-fitted within a bending moment absorber in the form of a strut assembly.
Figure 7B:
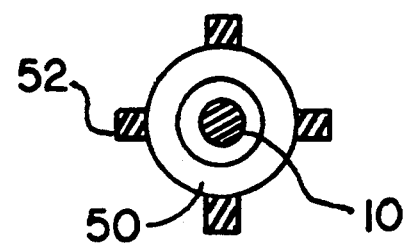
FIG. 7B is a cross-sectional view of FIG. 7A, shown for clarity.

FIG. 4A and FIG. 4B show the complete assembly where the bending moment absorber 12 and the dumbbell specimen 10 are grasped at each end by commercially available hydraulically-operated collet grips 18, for applying either static or dynamic forces in tension, compression, or torque, or a combination of these forces, as well as cyclic fatigue. The bending moment absorber 12 can be fabricated from any appropriate structural material including a polymer cast as a hollow cylinder around the specimen, having an inner diameter equal to that of the heads 14 of the specimen. As force is applied by a mechanical testing machine through the hydraulically-operated collet grips 18 to the bending moment absorber 12 and specimen heads 14, they are squeezed together and with pins 16 behave as an integral structure during testing. Alternatively, shrink-fitted or threaded joints, or mechanically or hydraulically activated jaws (not shown) and/or bonding, such as adhesive bonding, brazing or welding, can replace the pinned joints at the specimen head-ends, or a combination thereof can be employed. Similarly, as shown in FIG. 7A and FIG. 7B, a plurality of strut elements 52 joined by any of the present state-of-the-art joining methods that will bond in a rigid manner, such as welding 54 to hoops 50 fitted and fixed, by means previously described, to the head-ends 14 of the specimen can also be employed. Bending stresses caused by slight angular misalignment or eccentricities in the load train and within the specimen are effectively minimized by the marked increase in the moment of inertia provided by the bending moment absorber in the form of strut assembly, 50 and 52 acting in concert with the specimen 10.

Again referring to FIG. 4A and FIG. 4B, the axial strain can be monitored via electric-resistance strain gages 20 bonded to the bending moment absorber, or for elevated temperature operation, the axial displacement of the bending moment absorber 12 can be obtained using laser type extensometers (not shown). An additional extensometer can simultaneously be aimed through the ports 22 at the specimen gage diameter during elevated temperature operation. This allows the knowledge of the displacement or strain in the specimen 10 due to various modes of loading and temperature environments, and thus the stress as a function of temperature and the strength of the material can be determined. This is subsequently discussed in detail.

Figures 5A, 5B:
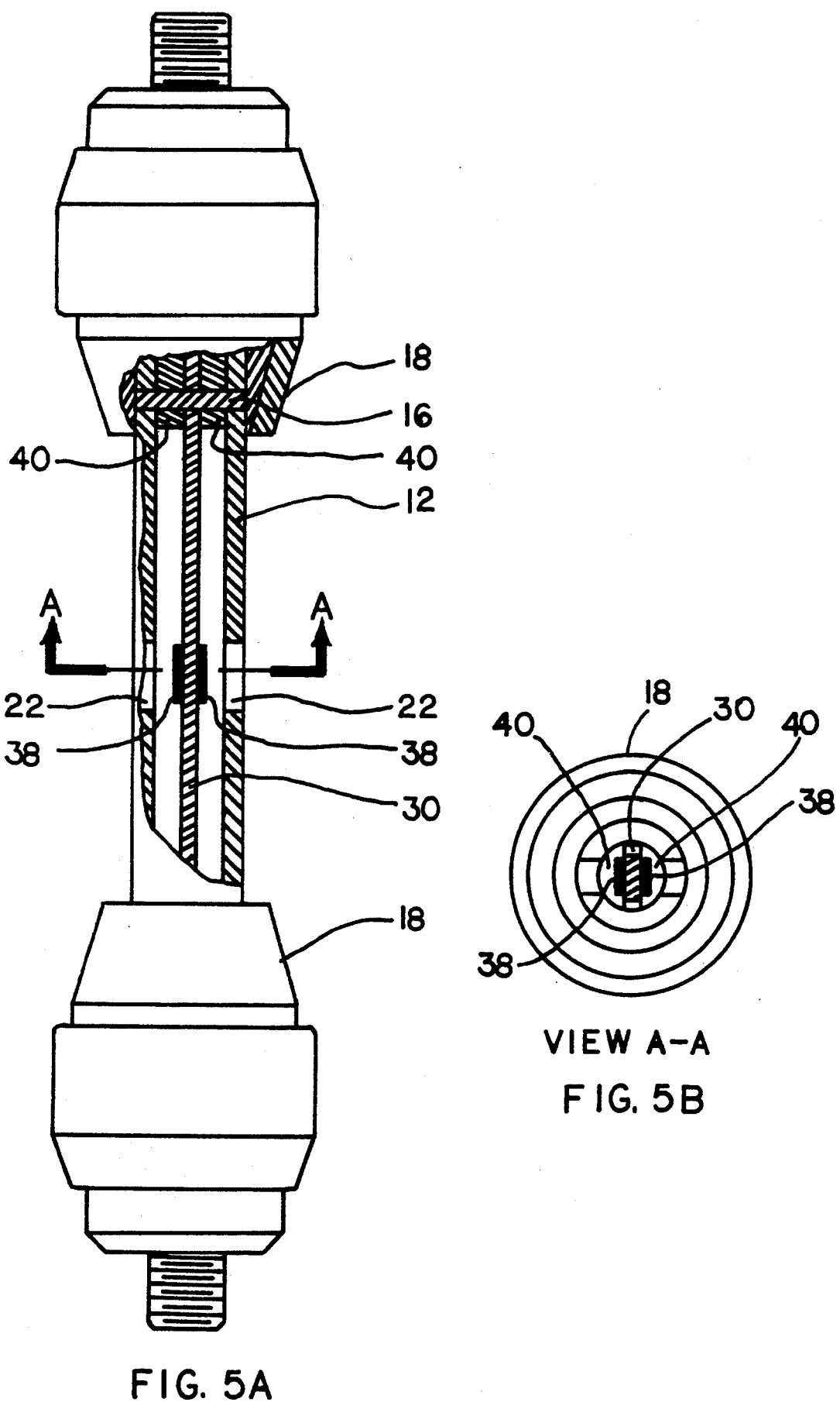
FIG. 5A is a cross-sectional view of a flat tensile specimen shown inserted and pinned with spacers within the bending moment absorber and this assembly, in turn, is grasped at both ends by hydraulically-operated collet grips.
FIG. 5B is a cross-sectional view of FIG. 5A, shown for clarity.

A flat tensile specimen, which can be stressed conveniently in only a tensile mode, can also be tested in an arrangement similar to that shown in FIG. 4A and FIG. 4B. Referring to FIG. 5A and FIG. 5B, which show the complete assembly, where the flat tensile specimen 30 is sandwiched at its ends by semi-cylindrical spacers 40 and pinned 16 or joined in the same ways described above at both ends (only one end is shown cross-sectioned) to the encompassing bending moment absorber 12; this in turn is grasped at its ends by a set of hydraulically-operated wedge grips 18. Again, strain gages on the bending moment absorber (not shown), or an extensometer can be used to obtain the strain in the moment absorber. The displacement of the flat specimen can be obtained by strain gages 38, or observed with an extensometer through the ports 22 of the moment absorber provided for that purpose.

To insure intimate contact during cryogenic temperature testing, the bending moment absorber material can be chosen such that its linear coefficient of thermal expansion is greater than that of the specimen material. At elevated temperatures the chosen thermal expansion ratio should be reversed. Ambient temperature testing will require a slip-fit between the bending moment absorber and the the specimen. The specimen material, the temperature at which testing is to be accomplished, and the ratio of the modulus of elasticity of the bending moment absorber to the specimen material will dictate the material to be used for the bending moment absorber. This was shown in the preferred embodiments above.

The test fixtures shown in FIG. 4A and FIG. 5A can be used for both static and dynamic loading at various temperature environments. However, even though dynamic loading with its required ancillary equipment and instrumentation can be an adjunct to the static fixtures, is not further discussed because it is not necessary to the understanding of the principle of the invention. Therefore, only static loading at various temperature environments are considered and discussed later. Nevertheless, such discussions are germane to the dynamic loading regime, as well.

Test Methods

The test device can be universally employed in the mechanical testing field within temperature regimes of interest: cryogenic, ambient, and at elevated temperatures. The device invented here can be readily adapted for testing at cryogenic temperatures through the use of a cold chamber or a refrigerated enclave (with observation ports) encompassing the bending moment absorber-specimen assembly. Such ancillary testing equipment is commercially available. Also, testing at elevated temperatures can be accomplished in a similar manner by utilizing, for example, a commercially available resistance-heated clamshell furnace (again with observation ports) mounted to the-load frame. Water cooled hydraulically-operated grips, which clamp the bending moment absorber-specimen assembly at each end, are also available for high temperature testing.

Such usage of the device, as mentioned above, with regard to the mechanics of materials behavior in at least two specific testing regimes, termed here the linear mode and the nonlinear mode, requires some discussion. Testing in the linear mode infers testing at temperatures where either the material behaves elastically or in a manner such that its stress-strain curve is linear. The limit of linearity is dependent upon the material, the applied stress and the temperature at which the specimen is exposed. A tensile specimen tested under either constant load or constant stress at a given temperature will exhibit time-dependent elongation; this is referred to as creep. At temperatures approximately less than 40 percent of the absolute melting point, the extent of creep is negligible; the linear mode. Above such a temperature regime is defined here as the nonlinear mode. It is seen therefore, that each material must be examined on an individual basis to determine the temperature at the onset of creep. The temperature at which creep initiates is well known for most structural materials, and if it is not known can be determined through the use of standard testing procedures. Testing with the present invention in the linear and the nonlinear regimes requires different testing procedures, each procedure is described in the paragraphs that follow.

a. Linear Regime

Again referring to FIG. 4A, when testing within the elastic regime or within the linear mode response of the material, the stress absorbed by the specimen 10 can be found for this situation in a different manner than that indicated by Eq. 11. This is accomplished in the following way: The strain gages 20 (or extensometers) on the bending moment absorber 12 are monitored, which allows the determination of the force Pa in the bending moment absorber. This is realized through the simple relationship between modulus of elasticity of the absorber Ea, the strain in the bending moment absorber $\epsilon a$ and the known cross-sectional area of the bending moment absorber Aa. The modulus of elasticity in this testing regime for most engineering materials, including brittle materials, is usually known through prior mechanical testing or ultrasonic techniques, and if not known can readily be determined. Therefore:

$$Pa = \epsilon a \, Aa \, Ea \tag{13}$$

Also, the total force in the system Pt is known from the commercially available mechanical testing machine to be used in conjunction with the integral bending moment absorber system. Thus, the force in-the specimen Ps is simply given by $$Ps = Pt - Pa \tag{14}$$

However, the desired quantity is the stress Ss in the test specimen, which is easily obtained since its cross-sectional area As is known:

$$Ss = Ps/As \qquad (15)$$

The engineering or true stress-true strain relationship of the test material can also be realized by monitoring the diameter displacement of the specimen 10 during testing, refer to FIG. 4A, via the use of visual extensometers sighting through the ports 22 in the bending moment absorber 12, or strain gages mounted on the specimen (not shown). During various modes of load application, i.e., tension, compression, shear and combinations thereof as well as fatigue, the failure strain in the specimen 10, and the failure strength of the material can be determined.

b. Nonlinear Regime

As previously mentioned, testing in the nonlinear mode where high temperature creep of the test material occurs requires a different approach than that described above. This is accomplished by fabricating the bending moment absorber out of the same material as the test specimen. With knowledge of the combined initial cross-sectional area of the bending moment absorber and the test specimen, the axial stresses in the specimen Ss and the absorber Sa are obtained from the simple engineering stress formula:

$$Ss = Sa = Pt/At \qquad (16)$$

Where as before Pt is the total load and At is the combined cross-sectional area of the bending moment absorber and the specimen.

If the specimen displacement is desired then extensometers aimed at the test specimen can be employed, rather than electric-resistance strain gages.

Alternatively, the system can be designed such that the specimen gage section is heated by an electric-resistance type heater. Additional access ports can be provided, if needed, in the bending moment absorber for the electric heater circuitry. Electric-resistance strain gages can be bonded to the bending moment absorber to monitor its strain during testing. The bending moment absorber will have a room temperature elastic modulus less than that of the specimen, and will be cooled so that it remains in the elastic regime during the test. Since this arrangement is well within the state-of-the art and not necessary to the understanding of the principle of the invention it is neither further described nor is it further detailed in a drawing.

The load sustained by the specimen and the stress can be determined in the following way:

The load in the specimen is given by Eq. 14, and the load absorbed by the bending moment absorber, where $\epsilon a$ is the strain in the bending moment absorber, is $$Pa = a\ Ea\ Aa = Sa\ Aa \qquad (17)$$

Since the bending moment absorber is cooled its modulus of elasticity is constant and known.

Substituting the relationship for Pa given above into Eq. 14 and dividing by As to obtain Ss results in the engineering stress $$Ss = (Pt - Sa\ Aa)/As \qquad (18)$$

If true stress-true strain is desired the instantaneous diameter of the specimen can be obtained via extensometer observations through access ports provided in the bending moment absorber.

The concepts and methods discussed above are equally applicable to those systems shown in FIG. 4A and FIG. 5A where a dumbbell and a flat tensile specimen are shown in each respective assembly.

I claim:

1. A method to determine mechanical properties of a material where a sample of said material is prepared for testing, said sample having a top end and a bottom end, top and bottom ends providing grip surfaces for a testing machine and said sample is then enclosed within surrounding means which has a upper end and a lower end; said surrounding means are then closely fitted to said sample top end and bottom end, and where, said top end of said sample is affixed by affixing means to the upper end of said surrounding means, and where said bottom end of said sample is affixed by affixing means to said lower end of said surrounding means, and where said sample and surrounding means are then clamped by clamping means within a testing device and when, the test device is then activated, the surrounding means, called a bending moment absorber, absorbs the bending moment of said sample reducing errors due to misalignment.

2. The claim in 1 where said sample behaves as a brittle material.

3. The claim in 2 where said surrounding means is a tube.

4. The claim in 2 where said surrounding means is a plurality of strut members affixed to hollow cylinder ends.

5. The claim in 2 where said affixing means is a pin or bolt.

6. The claim in 2 where said affixing means is an adhesive joint.

7. The claim in 2 where said affixing means is a shrink fit between the surrounding means and the top end of the sample and the surrounding means and the bottom end of the sample.

8. The claim in 2 where said affixing means is a threaded joint.

9. The claim in 2 where said affixing means is a soldered joint.

10. The claim in 2 where said affixing means is a brazed joint.

11. The claim in 2 where said affixing means is encapsulation within a cast or poured elastomer.

12. The claim in 2 where said clamping means are mechanically activated joints, such as two drillpress chuck mechanisms or two collet grips located or two hydraulically-operated grips at each end of the surrounding means, called a bending moment absorber.

13. The claim in 2 where said clamping means are two hydraulically-operated jaws located at each end of the surrounding means, called a bending moment absorber.

14. The claim in 2 where said surrounding bending moment absorber tube is a super alloy steel or a ceramic tube, thus allowing a functional bending moment absorbing method for high temperature tests of metals and ceramics.

15. The claim in 2 where said surrounding bending moment absorber tube material is chosen to have a linear coefficient of thermal expansion less than that of the prepared sample, such that a radial compression is provided at the top and bottom ends of the test sample when testing at elevated temperatures.

16. The claim in 2 where said surrounding bending moment absorber tube material is chosen to have a linear coefficient of thermal expansion greater than that of the prepared sample, such that a radial compression is provided at the top and bottom ends of the test sample when testing at cryogenic temperatures.

17. The claim in 2 where said surrounding bending moment absorber material is chosen to have a lower modulus of elasticity than that of the prepared sample, such that the sample will support a greater portion of the applied load and thus fail; leaving the bending moment absorber intact and allowing it to be reusable.

18. The claim in 2 where said surrounding bending moment absorber is used for static testing.

19. The claim in 2 where said surrounding bending moment absorber is used for dynamic testing.

20. The claim in 2 where said surrounding bending moment absorber is used for cyclic fatigue testing.

21. The claim in 2 where said surrounding bending moment absorber is used to apply a multiplicity of loadings, such as tension, compression, torque and a combination thereof.

22. A device to test materials that behave in a brittle fashion where a prepared sample, which has a top end and a bottom end enclosed within a surrounding sleeve which is called a bending moment absorber which has a top end and bottom end, where said prepared sample is affixed at the top end to the top end of said sleeve and where said prepared sample is affixed at the bottom end to the bottom end of said sleeve and where said top end of said sleeve is gripped by the top jaw of a testing machine and where bottom end of said sleeve is gripped by the bottom end of the bottom jaw of a testing machine, and where said surrounding sleeve, called a bending moment absorber, acts to align said top and bottom ends of said sample within said testing machine; preventing premature failure of said test sample.

23. A method to test materials that behave in a brittle fashion where a prepared test sample is enclosed within a closely conforming tubular sleeve, called a bending moment absorber, and affixed to the sleeve at each end, and where the ends of the tubular sleeve and the contained sample are gripped within a testing machine, where the the tubular sleeve provides additional moment of inertia to the said prepared test sample it encloses and reduces the effect of the inherent misalignment.

* * * * *

UNITED STATES PATENT AND TRADEMARK OFFICE
CERTIFICATE OF CORRECTION

PATENT NO. : 5,431,062
DATED : July 11, 1995
INVENTOR(S) : Francis I. Baratta

It is certified that error appears in the above-indentified patent and that said Letters Patent is hereby corrected as shown below:

In column 10, delete [line36] and replace with:

$$Ssb = 4Pt\,e/\{Rs\,As\,[1 + (Ro/Rs)^4 - (Ri/Rs)^4]\} \qquad (10)$$

In column 10, delete [line 45} and replace with:

$$Ss = (4Pt/As)/\{1 + (Ea/Es)\,[(Ro/Rs)^2 - (Ri/Rs)^2]\} \qquad (11)$$

In column 10, delete [line51 and 52] and replace with:

$$\%Error = 100x(4e/Rs)\{1 + (Ea/Es)\,[(Ro/Rs)^2 - (Ri/Rs)^2]\}/[1+ (Ro/Rs)^4 - (Ri/Rs)^4] \qquad (12)$$

Signed and Sealed this

Thirteenth Day of February, 1996

*Attest:*

BRUCE LEHMAN

*Attesting Officer*   Commissioner of Patents and Trademarks